(12) United States Patent
David

(10) Patent No.: US 8,127,778 B1
(45) Date of Patent: Mar. 6, 2012

(54) DENTAL FLOSS DEVICE

(76) Inventor: Yair David, Ramat Hasharon (IL)

( * ) Notice: Subject to any disclaimer, the term of this patent is extended or adjusted under 35 U.S.C. 154(b) by 0 days.

(21) Appl. No.: 12/901,536

(22) Filed: Oct. 10, 2010

(51) Int. Cl.
*A61C 15/00* (2006.01)

(52) U.S. Cl. ...................................................... 132/321

(58) Field of Classification Search .................. 132/309, 132/311, 314, 321, 323, 327, 329; 206/63.5, 206/368, 227, 388, 49
See application file for complete search history.

(56) References Cited

U.S. PATENT DOCUMENTS

| | | | | |
|---|---|---|---|---|
| 546,127 | A * | 9/1895 | Armstrong | 206/388 |
| 3,831,611 | A | 8/1974 | Hendricks | |
| 4,040,433 | A * | 8/1977 | Edison | 132/321 |
| 4,403,625 | A * | 9/1983 | Sanders et al. | 132/323 |
| 4,852,728 | A * | 8/1989 | Court | 206/63.5 |
| 4,986,289 | A * | 1/1991 | McWhorter | 132/323 |
| 5,050,625 | A * | 9/1991 | Siekmann | 132/323 |
| 5,102,332 | A * | 4/1992 | Uthoff | 433/6 |
| 5,174,314 | A | 12/1992 | Charatan | |
| 5,322,077 | A * | 6/1994 | Corella | 132/323 |
| 5,406,965 | A * | 4/1995 | Levine | 132/323 |
| 5,454,386 | A * | 10/1995 | Dix | 132/323 |
| 5,503,168 | A | 4/1996 | Wang | |
| 5,549,201 | A * | 8/1996 | Braude | 206/388 |
| 5,566,692 | A * | 10/1996 | Thornton | 132/324 |
| 5,582,194 | A * | 12/1996 | Dolan | 132/321 |
| 5,692,610 | A * | 12/1997 | Porteous | 206/388 |
| 5,735,299 | A * | 4/1998 | Kaltenbach | 132/323 |
| 5,794,776 | A * | 8/1998 | Corella | 206/388 |
| 5,890,500 | A | 4/1999 | Mabon et al. | |
| 5,913,418 | A * | 6/1999 | Singh | 206/63.5 |
| 5,915,392 | A * | 6/1999 | Isaac | 132/200 |
| 6,102,051 | A * | 8/2000 | Neves | 132/321 |
| 6,220,257 | B1 * | 4/2001 | Meyer et al. | 132/323 |
| 6,234,182 | B1 * | 5/2001 | Berglund | 132/323 |
| 7,665,600 | B1 * | 2/2010 | Griffin | 206/63.5 |
| 2004/0065342 | A1 | 4/2004 | Sherman | |
| 2004/0168703 | A1* | 9/2004 | Cho | 132/323 |
| 2005/0006263 | A1* | 1/2005 | Tsaur | 206/368 |
| 2005/0115854 | A1* | 6/2005 | Miles | 206/368 |
| 2007/0277845 | A1* | 12/2007 | Blasco | 132/321 |
| 2010/0139688 | A1* | 6/2010 | Musgrave | 132/321 |

FOREIGN PATENT DOCUMENTS

GB 2289845 A 12/1995

* cited by examiner

*Primary Examiner* — Todd Manahan
*Assistant Examiner* — Tatiana Nobrega

(57) ABSTRACT

A method and a dental floss device for floss the teeth of a user, in accordance with an embodiment of the present invention. The dental floss device includes a single use dental floss packaged inside a dental tubule.

13 Claims, 5 Drawing Sheets

DENTAL FLOSS DEVICE

FIELD OF THE INVENTION

The present invention relates to oral hygiene, more particularly, to single use dental floss, and more particularly, to a dental floss device including dental floss packaged within a tubule.

BACKGROUND OF THE INVENTION

To maintain dental hygiene, it is important to clean the teeth every so often, and to remove food remnants from between the teeth. At present, various means are used for this purpose, dental floss being one of the most efficient means currently available. One particularly popular means is lengths of waxed dental floss, contained within a dispenser, wound onto a spool, with one end protruding slightly. In preparation for use, the user pulls the end of the dental floss, exposing the desired length of floss from the dispenser, and then cuts it and uses it.

The length of the dental floss contained within the dispenser can be, for example, 50 meters. A typical length of the length cut for the purpose of use can be approximately 30 centimeters.

There are many situations in which a user knows that there will be a need for a single-use package of dental floss, such as for example, when going out to a restaurant and continuing straight on from there to another event. In this case, carrying a dispenser with an unnecessary length of floss is inconvenient.

In order to meet the need for a small and convenient means of dental flossing, several solutions have been propose, such as a fork-like device with two prongs and a short length of dental floss stretched between them. However, those who prefer a more thorough cleaning with the dental floss wound on their own fingers, one from each hand, do not find such solutions satisfactory.

Packages of short pieces of dental floss for single use have also been proposed.

An oral hygiene device, which is a disposable single use package, is described in U.S. Pat. No. 4,852,728 of Court.

FIG. 1 of the prior art illustrates the disposable single use package 60 of Court.

The single use package 60 includes a dental floss 10 at a length suitable for single use, a first triangularly shaped leaf 61 and a second triangularly shaped leaf 62. The first triangularly shaped leaf 61 and the second triangularly shaped leaf 62 are connected to each other by means of a common ridge. When in storage, they are folded onto each other, and prior to use, they are opened, to enable removal of the dental floss 10.

A single use dental floss dispenser is described in U.S. Pat. No. 5,582,194 of Dolan.

FIG. 2 of the prior art illustrates the single use dental floss dispenser 70 of Dolan.

The single use dental floss dispenser 70 of Dolan includes a dental floss 10 at a length suitable for single use, disposed within a cover portion 71, which is closed for storage by means of a lid portion 72. The lid portion 72 is opened prior to use, to enable removal of the dental floss 10.

In spite of all of the known and existent solutions, there is still a need for a short length of dental floss, conveniently packaged for single use. It is possible to simply pre-cut a short length of dental floss and store it in one's pocket, until it is removed from the pocket for use. This would be the most convenient solution in terms of storage, volume, and weight; however, in this manner the dental floss cannot be kept sufficiently clean, and can cause infections in the user's mouth.

None of the prior art devices comprises all of the above characteristics and functions.

There is therefore a need for a device including a short length of dental floss, for single use, whose size, volume, weight, and pliability are similar to those of bare dental floss, while maintaining sanitary conditions during carrying in the user's pocket. Such a device would be suitable for use at restaurants and other such businesses and venues, similarly to toothpicks provided in a suitable dispenser on the table or countertop.

SUMMARY OF THE INVENTION

The background art does not teach or suggest a short length of single use dental floss, which is contained in a protective package prior to use, the package adding minimal weight and volume, thus enabling convenient carrying, with the contained dental floss, in one's pocket.

The present invention overcomes these deficiencies of the background art by providing a short length of dental floss contained within a tubule.

According to the teaching of the present invention there is provided a dental floss device, the dental floss device including: (a) a dental tubule having a dental tubule first end, a dental tubule second end, a dental tubule interior diameter, a dental tubule outer diameter, a dental tubule length, and a dental tubule weight; and (b) a dental floss having a dental floss first end, a dental floss second end, a dental floss length, a dental floss outer diameter, and a dental floss weight, wherein most of the dental floss contained inside the dental tubule.

According to another feature of an embodiment of the present invention the dental floss has an exposed segment.

According to another feature of an embodiment of the present invention the dental tubule has an open end and a closed end.

According to another feature of an embodiment of the present invention the dental tubule has an empty segment.

According to another feature of an embodiment of the present invention the dental tubule interior diameter is substantially larger than the dental floss outer diameter.

According to another feature of an embodiment of the present invention the dental tubule interior diameter is substantially equal to the dental floss outer diameter.

According to another feature of an embodiment of the present invention there is an overlapping zone between the dental tubule and the dental floss, and wherein the dental tubule is substantially pressing on the dental floss along the entire overlapping zone.

According to another feature of an embodiment of the present invention the dental tubule is substantially pressing on the dental floss at most on ten percent of the overlapping zone.

According to another feature of an embodiment of the present invention in order to pull out the dental floss from the dental tubule there is a need to apply a force.

According to another feature of an embodiment of the present invention the force has at least a predetermined force value.

According to another feature of an embodiment of the present invention the force has a value of at least twice of the dental floss weight value.

According to another feature of an embodiment of the present invention the force has at least a value of twice of the dental tubule weight value.

According to another feature of an embodiment of the present invention the dental tubule is made of material enabling bending the dental tubule at a bending radius smaller than five millimeter.

According to another feature of an embodiment of the present invention the dental floss device further includes: (c) a cap, wherein the cap is mounted on the exposed segment.

According to another feature of an embodiment of the present invention the dental tubule is made of material selected from a group consisting of polyisoprene, latex, and polyurethane.

According to the teaching of the present invention there is provided a method for using a dental floss to floss teeth of a user, in accordance with an embodiment of the present invention, the method including the stages of: (a) gripping with one hand an exposed segment of a dental floss, and gripping with the other hand an empty segment of a dental tubule; (b) pulling the exposed segment of the dental floss, and pulling with the other hand the empty segment of the dental tubule in an opposite direction; (c) extracting the dental floss from the dental tubule; and (d) cleaning between the teeth, with the dental floss that was extracted.

Additional objects and advantages of the invention will be set forth in part in the description which follows and, in part, will be obvious from the description, or may be learned by practice of the invention.

BRIEF DESCRIPTION OF THE DRAWINGS

The invention is herein described, by way of example only, with reference to the accompanying drawings, wherein.

DETAILED DESCRIPTION OF EMBODIMENTS OF THE INVENTION

Figure 1:
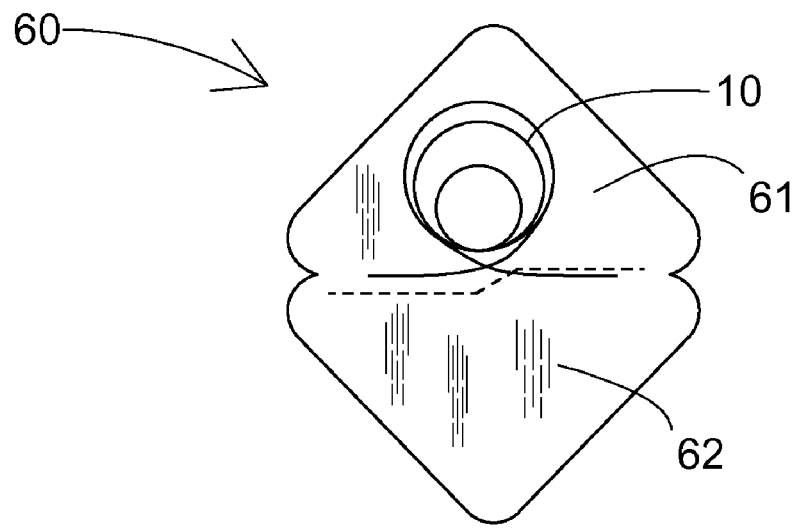
FIG. 1 of the prior art illustrates a disposable single use package.
Figure 2:
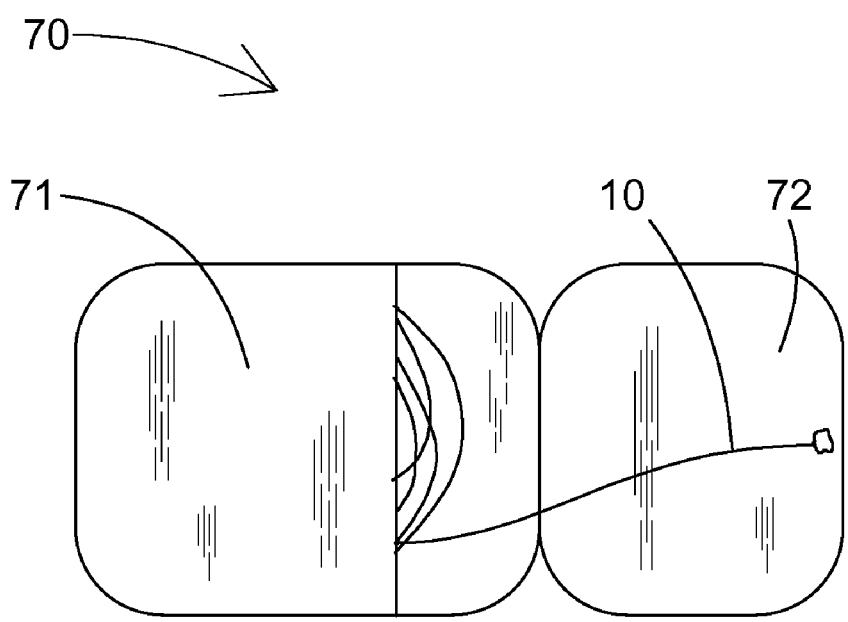
FIG. 2 of the prior art illustrates a single use dental floss dispenser.

The present invention is of a dental floss device. The principles and operation of a dental floss device according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

As used herein the specification and in the claims section that follows, the term 'single use' refer to a use of the dental floss device for cleaning in one session between the teeth of a user.

This definition is to distinguish this use from that of a long length of dental floss, from which dental floss is occasionally cut at the desired length for cleaning between the teeth, with the long length of dental floss being able to be cut many times, until there is not enough dental floss left for use.

As used herein the specification and in the claims section that follows, the term 'dental tubule' refer to a tubule having suitable qualities for use as a component of a dental floss device, according to the present invention.

The following list is a legend of the numbering of the application illustrations:

| | |
|---|---|
| 10 | dental floss |
| 10a | dental floss first end |
| 10b | dental floss second end |
| 101 | dental floss length |
| 10od | dental floss outer diameter |
| 10W | dental floss weight |
| 11 | exposed segment |
| 20 | dental tubule |
| 20a | dental tubule first end |
| 20b | dental tubule second end |
| 20id | dental tubule interior diameter |
| 201 | dental tubule length |
| 20od | dental tubule outer diameter |
| 20W | dental tubule weight |
| 21 | empty segment |
| 25 | cap |
| 27 | overlapping zone |
| 29 | bending radius |
| 31 | local gap |
| 401 | left hand |
| 40r | right hand |
| 50 | threading device |
| 51 | hook |
| 60 | disposable single use package, (prior art, according to Court) |
| 61 | first triangularly shaped leaf, (prior art, according to Court) |
| 62 | second triangularly shaped leaf, (prior art, according to Court) |
| 70 | dental floss dispenser, (prior art, according to Dolan) |
| 71 | cover portion, (prior art, according to Dolan) |
| 72 | lid portion, (prior art, according to Dolan) |
| 100 | dental floss device |
| F | force |

Hereinafter, embodiments of the present invention are explained in detail by referring to the drawings.

Figure 3A:
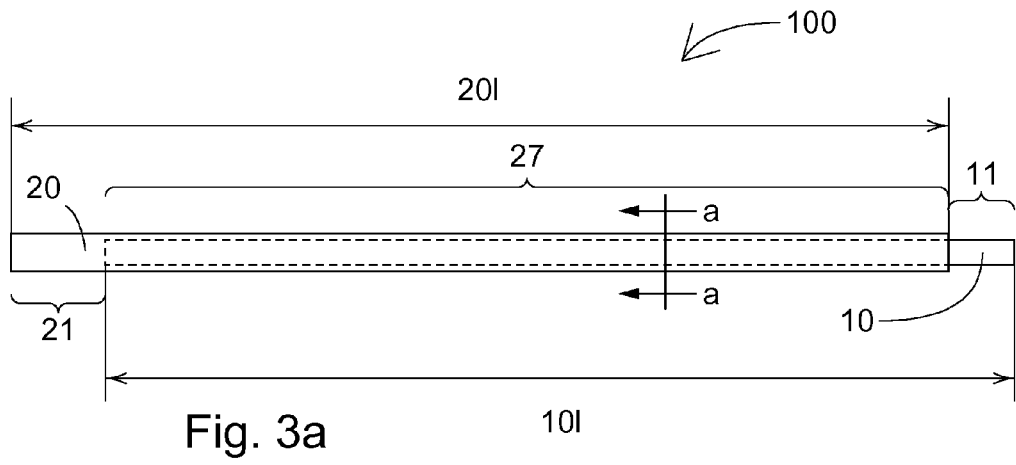
FIG. 3a is a side view schematic illustration of a dental floss device, in accordance with an embodiment of the present invention, upon which a section plane a-a is marked.

FIG. 3a is a side view schematic illustration of a dental floss device 100, in accordance with an embodiment of the present invention, upon which a section plane a-a is marked.

The present illustration shows a state of storage and carrying of the dental floss device 100, however for the purpose of clarity, it is shown straight, without any folds.

A dental floss 10 having a dental floss length 101 is mostly disposed within a dental tubule 20. A minimal value of dental floss length 101 to enable an adult's use of dental floss 10 should be no shorter than 10 centimeters.

The value of dental floss length 101 above which there is a superfluous waste of dental floss 10 is no longer than 40 centimeters.

The dental tubule 20 has a dental tubule length 201, is open at one end, and closed at the other end, to prevent infiltration of contaminants.

The dental floss 10 has an exposed segment 11, which serves the purpose of enabling the fingers of one hand of the user to grasp it, when pulling from the dental tubule 20, and the dental tubule 20 has an empty segment 21, which serves the purpose of enabling the fingers of the other hand of the user to grasp it when pulling. The segment of the dental tubule 20 containing the dental floss 10 is referred to as an overlapping zone 27. The overlapping zone 27 is at its largest during storage, and becomes smaller when pulling dental floss 10, and does not exist at all when the pulling is completed.

For the purpose of clarity of details, the present illustration, as well as some of the following illustrations, shows the dental floss 10 and the dental tubule 20 with exaggeratedly large diameters in proportion to their lengths, relative to their actual proportions.

The dental tubule 20 is designated to maintain the hygiene of the dental floss 10 contained within. The necessary features of the dental tubule 20 are imperviousness to contaminants and, as far as possible, not to create any bending restrictions, which do not apply to the dental floss 10 itself, while being strong enough to be resistant to tearing. Its structural material and dimensions should be selected accordingly. Possible materials also include plastic materials. The structural materials can be materials without any stretching qualities, or with stretching qualities such as polyisoprene, which is a natural polymer, strong and elastic, inert, and does not cause allergic reactions.

Additional suitable material also include latex, and polyurethane.

However, these materials are in no way limiting the present invention.

Figure 3B:
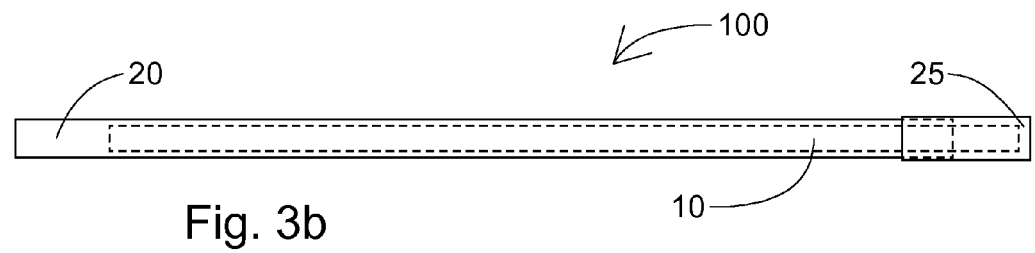
FIG. 3b is a side view schematic illustration of a dental floss device, including a cap, in accordance with an embodiment of the present invention.

FIG. 3b is a side view schematic illustration of a dental floss device 100, including a cap 25, in accordance with an embodiment of the present invention.

The addition of cap 25 improves the sterility of the dental floss 10.

Figure 4:
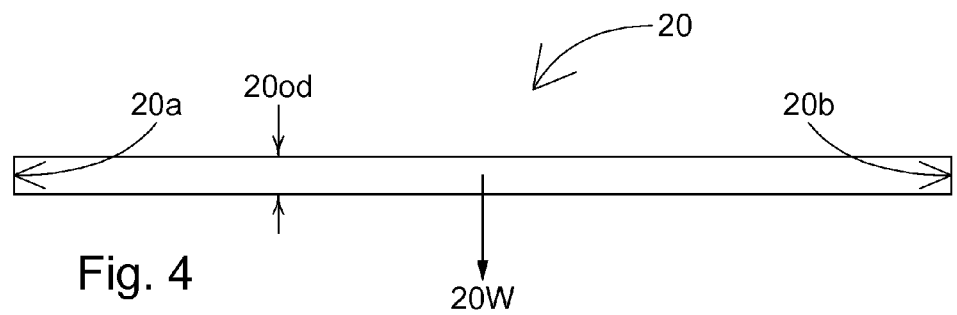
FIG. 4 is a side view schematic illustration of a dental tubule of the dental floss device, in accordance with an embodiment of the present invention.

FIG. 4 is a side view schematic illustration of a dental tubule 20 of the dental floss device 100, in accordance with an embodiment of the present invention.

Dental tubule 20 has a dental tubule first end 20a, a dental tubule second end 20b, a dental tubule outer diameter 20od, and a dental tubule weight 20W.

Figure 5:
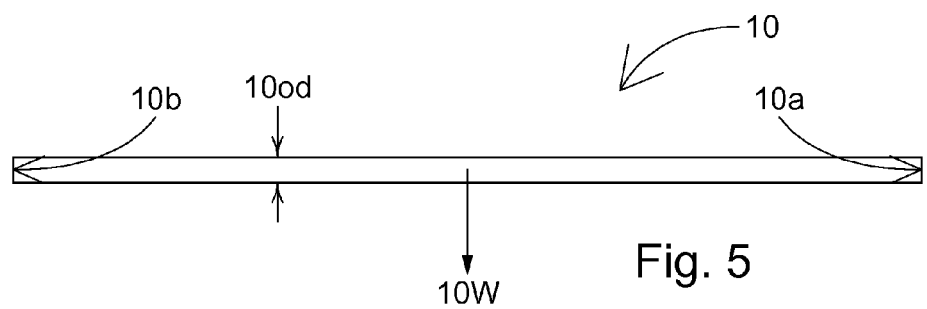
FIG. 5 is a side view schematic illustration of a dental floss of the dental floss device, in accordance with an embodiment of the present invention.

FIG. 5 is a side view schematic illustration of a dental floss 10 of the dental floss device 100, in accordance with an embodiment of the present invention.

The dental floss 10 has a dental tubule first end 10a, a dental tubule second end 10b, a dental floss outer diameter 10od, and a dental floss weight 10W.

Figure 6:
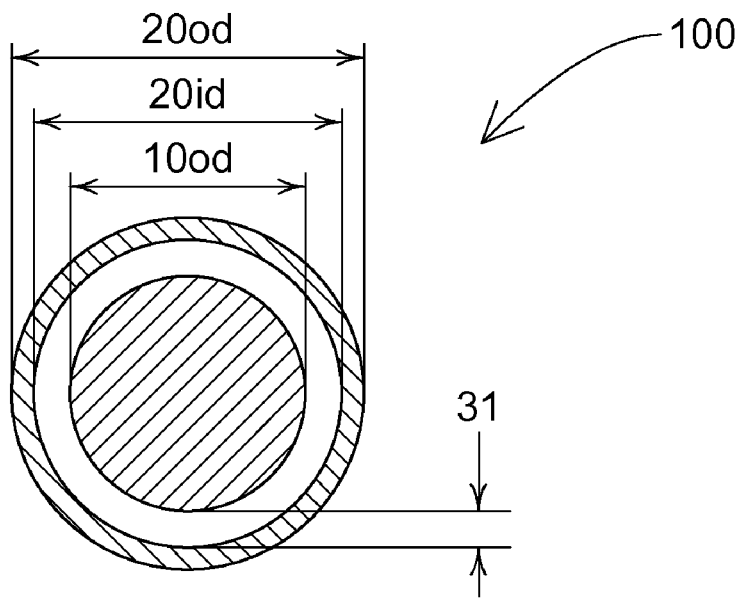
FIG. 6 is a cross sectional view a-a of a dental floss device, in accordance with an embodiment of the present invention.

FIG. 6 is a cross sectional view a-a of a dental floss device 100, in accordance with an embodiment of the present invention.

The dental floss 10 has also a dental tubule interior diameter 20id.

A local gap 31, the value of which can vary in different locations along the cross section, and along the overlapping zone 27, (not shown in the present illustration, shown in FIG. 3a) can exist between the dental floss 10 and the dental tubule 20.

Figure 7:
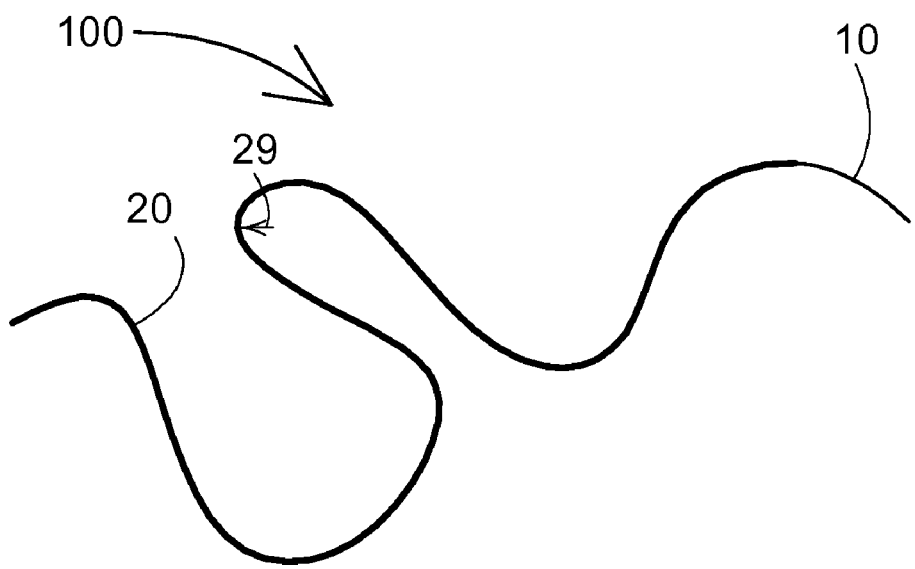
FIG. 7 is a top view schematic illustration of a dental floss device, in accordance with an embodiment of the present invention.

FIG. 7 is a top view schematic illustration of a dental floss device 100, in accordance with an embodiment of the present invention.

The illustration demonstrates the torsion of the dental floss device 100.

A bending radius 29, no larger than 5 millimeters, is sufficient for all practical purposes of carrying the dental floss device 100.

A quantity of dental floss devices 100 can be packaged, for the purpose of sale, in bags or boxes, or can be sold in bulk.

Figure 8:
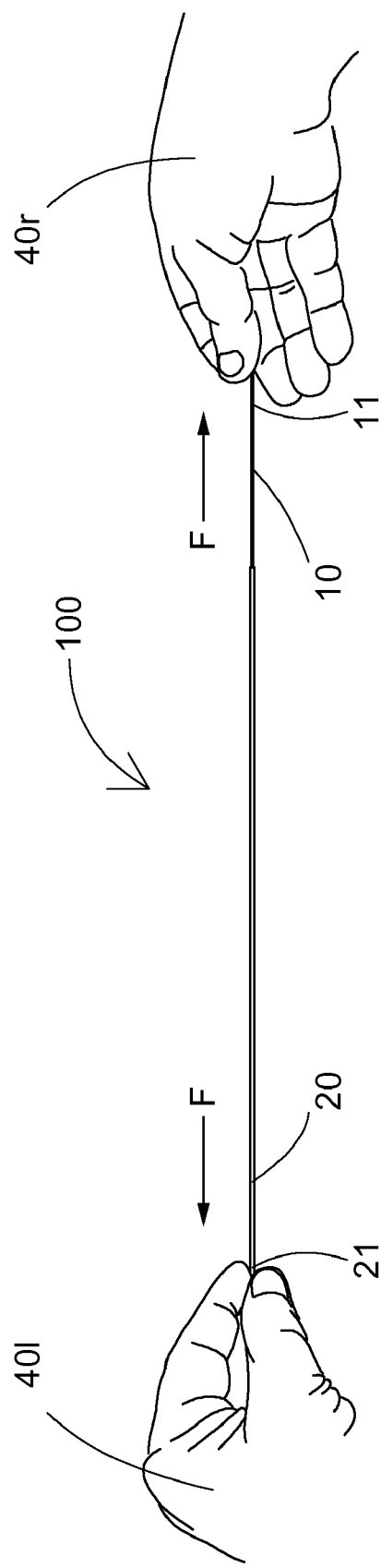
FIG. 8 is a side view schematic illustration of two hands performing an operating stage of the dental floss device, in accordance with an embodiment of the present invention.

FIG. 8 is a side view schematic illustration of two hands performing an operating stage of the dental floss device 100, in accordance with an embodiment of the present invention.

In the case shown in the present illustration, the left hand 40l grips the empty segment 21, the right hand 40r grips the exposed segment 11, and each one pulls with force F for the purpose of removal. The force required for removal grows smaller as the removal progresses. The necessary force is determined also by the friction coefficient, the compacting force, if existent, applied by the dental tubule 20 on the dental floss 10 and the length of the overlapping zone 27 (indicated in FIG. 3a).

The necessary force F must not be too small, in order to prevent accidental removal, but must also not be so large as to pose difficulty during removal and to risk tearing the dental tubule 20 during removal. Therefore, the design and production of the dental floss device 100 are performed so that the necessary force F will be in the range between two predetermined values.

A reasonable minimal value of force F, under which removal will not occur, which is the larger of twice the dental tubule weight 20W and twice the dental floss weight 10W.

Figure 9:
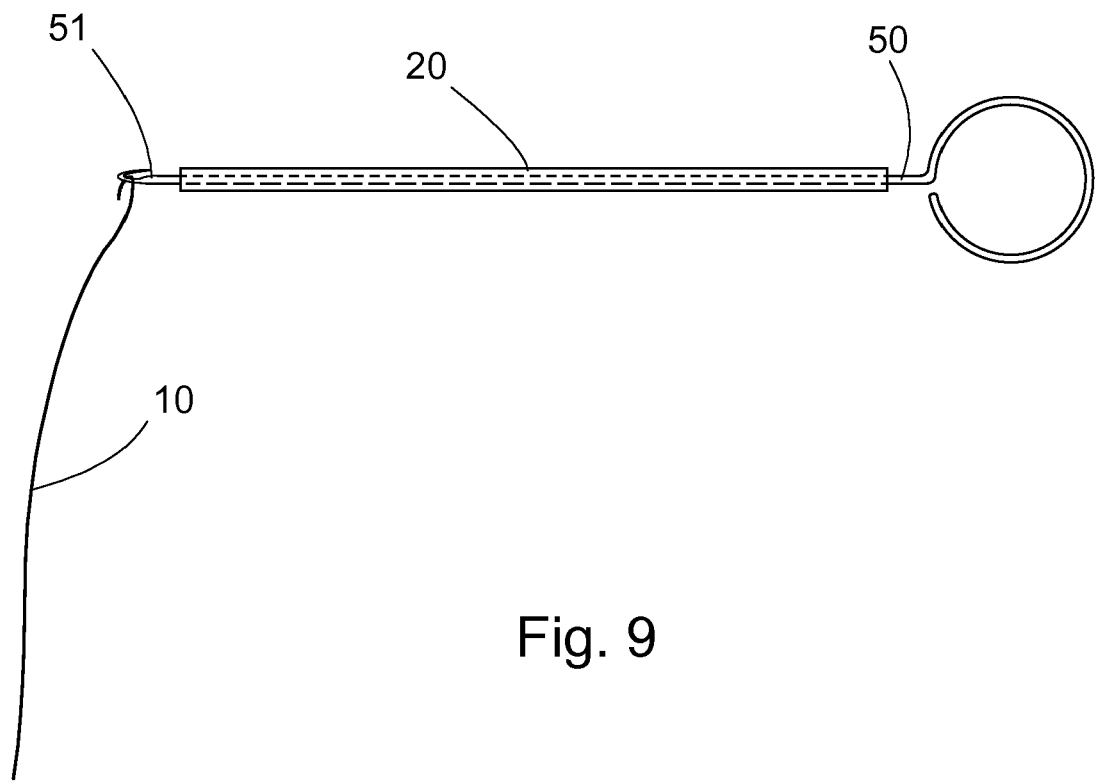
FIG. 9 is a side view schematic illustration of a threading device, dental tubule, and a dental floss, in accordance with an embodiment of the present invention.

FIG. 9 is a side view schematic illustration of a threading device 50, dental tubule 20, and a dental floss 10, in accordance with an embodiment of the present invention.

The present illustration shows a stage in one possible production process of the dental floss device 100, according to the present invention.

A hook 51 of a threading device 50, threaded through dental tubule 20 is connected to dental floss 10, which will be later pulled and threaded through the dental tubule 20.

There is a range of options for the measure of compacting force activated by the dental tubule 20 on the dental floss 10, starting from no compacting at all, through a state of compacting resulting from the use of a narrow dental tubule 20, a state of compacting as a result of use of a narrow dental tubule 20 made of elastic material, to performing a shrink wrap of the dental tubule 20 after completion of threading.

Another good option is to create a state of compacting along only a short segment in close proximity to dental floss second end 10b (indicated on FIG. 5). This possibility is advantageous in that only at the beginning of the removal process is there a need for force, and most of the length of dental floss 10 does not come into contact almost at all with the internal wall of the dental tubule 20 so that if it is coated with or immersed in materials, they will not be diminished in the removal process.

Figure 10:
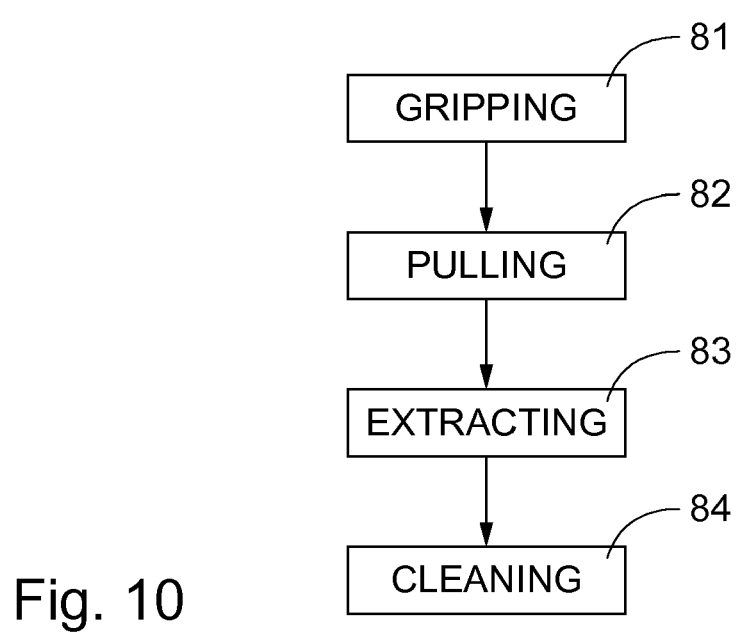
FIG. 10 is a flow chart that schematically illustrates a method for using dental floss to floss the teeth of a user, in accordance with an embodiment of the present invention.

FIG. 10 is a flow chart that schematically illustrates a method for of using a dental floss to floss tooth of a user, in accordance with an embodiment of the present invention.

The method includes the stages of:

gripping with one hand the exposed segment of a dental floss, and gripping with the other hand an empty segment of a dental tubule, (stage 81);

pulling the exposed segment of a dental floss, and pulling with the other hand the empty segment of a dental tubule in an opposite directions, (stage 82);

extracting the dental floss from the dental tubule, (stage 83); and cleaning between the teeth, with the dental floss that was extracted, (stage 84).

While the invention has been described with respect to a limited number of embodiments, it will be appreciated that many variations, modifications and other applications of the invention may be made.

What is claimed is:

1. A dental floss device comprising: a dental tubule having a closed first end, an open second end, a dental tubule interior diameter, a dental tubule outer diameter, a dental tubule length and a dental tubule weight; and a dental floss having a dental floss first end, a dental floss second end, a dental floss length approximately equal to the length of the dental tubule, a dental floss outer diameter, and a dental floss weight, wherein most of the dental floss is contained in the dental tubule and said dental floss has an exposed segment which extends longitudinally beyond the second end of the dental tubule and into a cap mounted on said exposed segment of floss where the cap surrounds and encloses said exposed segment of floss.

2. The dental floss device of claim 1, wherein said dental tubule has an empty segment.

3. The dental floss device of claim 2, wherein said dental tubule interior diameter is substantially larger than said dental floss outer diameter.

4. The dental floss device of claim 2, wherein said dental tubule interior diameter is substantially equal to said dental floss outer diameter.

5. The dental floss device of claim 2, wherein there is an overlapping zone between said dental tubule and said dental floss, and wherein said dental tubule is substantially pressing on said dental floss along the entire of said overlapping zone.

6. The dental floss device of claim 2, wherein there is an overlapping zone between said dental tubule and said dental floss, and wherein said dental tubule is substantially pressing on said dental floss at most on ten percent of said overlapping zone.

7. The dental floss device of claim 2, wherein in order to pull out said dental floss from said dental tubule there is a need to apply a force.

8. The dental floss device of claim 7, wherein said force has at least a predetermined force value.

9. The dental floss device of claim 7, wherein said force has at least a value twice of said dental floss weight value.

10. The dental floss device of claim 7, wherein said force has at least a value of twice said dental tubule weight value.

11. The dental floss device of claim 2, wherein said dental tubule is made of material enabling bending said dental tubule at a bending radius smaller than five millimeter.

12. The dental floss device of claim 2, wherein said dental tubule is made of material selected from a group consisting of polyisoprene, latex, and a polyurethane.

13. A method of using the dental floss device of claim 1 to floss a user's teeth, the method comprising the stages of:
   (a) gripping with one hand an exposed segment of a dental floss, and gripping with the other hand an empty segment of a dental tubule;
   (b) pulling with one hand said exposed segment of said dental floss, and pulling with the other hand said empty segment of said dental tubule in an opposite directions;
   (c) extracting said dental floss from said dental tubule; and
   (d) cleaning between the teeth, with said dental floss that was extracted.

* * * * *